US009072478B1

(12) United States Patent
Feerst

(10) Patent No.: US 9,072,478 B1
(45) Date of Patent: Jul. 7, 2015

(54) SYSTEM AND METHOD FOR IMPROVING PRESENTATION SKILLS

(71) Applicant: AutismSees LLC, Mount Pleasant, SC (US)

(72) Inventor: Danielle Alexis Feerst, Mount Pleasant, SC (US)

(73) Assignee: AutismSees LLC, Mount Pleasent, SC (US)

( * ) Notice: Subject to any disclaimer, the term of this patent is extended or adjusted under 35 U.S.C. 154(b) by 0 days.

(21) Appl. No.: 14/300,653

(22) Filed: Jun. 10, 2014

Related U.S. Application Data

(60) Provisional application No. 61/833,303, filed on Jun. 10, 2013.

(51) Int. Cl.
| | |
|---|---|
| *G09B 19/04* | (2006.01) |
| *A61B 5/16* | (2006.01) |
| *G09B 7/02* | (2006.01) |
| *G09B 5/06* | (2006.01) |
| *G09B 17/00* | (2006.01) |
| *G09B 17/02* | (2006.01) |
| *G09B 17/04* | (2006.01) |
| *A61B 3/113* | (2006.01) |

(52) U.S. Cl.
CPC ... *A61B 5/16* (2013.01); *G09B 7/02* (2013.01); *G09B 5/06* (2013.01); *G09B 5/065* (2013.01); *G09B 17/00* (2013.01); *G09B 17/02* (2013.01); *G09B 17/04* (2013.01); *G09B 17/003* (2013.01); *G09B 17/006* (2013.01); *G09B 19/04* (2013.01); *A61B 5/165* (2013.01); *A61B 5/167* (2013.01); *A61B 5/168* (2013.01); *A61B 3/113* (2013.01)

(58) Field of Classification Search
CPC .......... A61B 5/16; A61B 5/165; A61B 5/167; A61B 5/168; A61B 3/113; G09B 5/06; G09B 5/065; G09B 17/00; G09B 17/02; G09B 17/04; G09B 17/003; G09B 17/006; G09B 19/04; G09B 23/28
USPC ......... 434/235, 236, 308, 319, 320, 156, 167, 434/178, 185; 600/558
See application file for complete search history.

(56) References Cited

U.S. PATENT DOCUMENTS

| | | | | |
|---|---|---|---|---|
| 6,045,515 | A * | 4/2000 | Lawton | 600/558 |
| 6,644,973 | B2 * | 11/2003 | Oster | 434/178 |
| 6,931,587 | B1 * | 8/2005 | Krause | 715/205 |
| 7,211,050 | B1 * | 5/2007 | Caplygin | 600/558 |
| 7,678,047 | B2 * | 3/2010 | Shiomi et al. | 600/300 |
| 7,815,507 | B2 * | 10/2010 | Parrott et al. | 463/36 |
| 7,972,278 | B2 * | 7/2011 | Graham et al. | 600/558 |
| 8,048,002 | B2 * | 11/2011 | Ghajar | 600/558 |

(Continued)

*Primary Examiner* — Nikolai A Gishnock
(74) *Attorney, Agent, or Firm* — Goodwin Procter LLP

(57) ABSTRACT

A system and method for improving social and presentation skills of persons with a social communication disorder such as Autism. Social anxiety or a lack of confidence, the method including: rendering and displaying on a display device a presentation script for an oral presentation to be made by a user; monitoring eye movement of the user during the oral presentation to measure a user's pupil movement and/or a user's gaze direction; displaying an indicia on a separate display screen and/or an upper portion of the display device; periodically displaying within the presentation script a visual prompt to cue the user to look at the indicia; measuring eye movement using eye tracking software and/or an eye tracking device, at occurrence of the visual prompt; and evaluating whether the user made eye contact with the indicia when prompted.

23 Claims, 4 Drawing Sheets

(56) References Cited

U.S. PATENT DOCUMENTS

| | | | |
|---|---|---|---|
| 8,454,165 B2 * | 6/2013 | Duffy | 351/239 |
| 8,465,153 B1 * | 6/2013 | Bruun-Jensen et al. | 351/232 |
| 8,475,391 B2 * | 7/2013 | Duffy | 600/558 |
| 8,562,541 B2 * | 10/2013 | Duffy | 600/558 |
| 8,602,789 B2 * | 12/2013 | Hallowell et al. | 434/167 |
| 8,740,794 B2 * | 6/2014 | Scott | 600/301 |
| 8,752,964 B1 * | 6/2014 | Bruun-Jensen et al. | 351/232 |
| 8,777,630 B2 * | 7/2014 | Duffy | 434/236 |
| 2001/0046659 A1 * | 11/2001 | Oster | 434/178 |
| 2002/0099305 A1 * | 7/2002 | Fukushima et al. | 600/558 |
| 2005/0273017 A1 * | 12/2005 | Gordon | 600/544 |
| 2006/0093998 A1 * | 5/2006 | Vertegaal | 434/236 |
| 2006/0270945 A1 * | 11/2006 | Ghajar | 600/558 |
| 2007/0050151 A1 * | 3/2007 | Satoh et al. | 702/19 |
| 2007/0166676 A1 * | 7/2007 | Bird et al. | 434/236 |
| 2007/0248938 A1 * | 10/2007 | Ronald | 434/178 |
| 2009/0051877 A1 * | 2/2009 | Delahunt et al. | 351/246 |
| 2010/0092929 A1 * | 4/2010 | Hallowell et al. | 434/167 |
| 2011/0026779 A1 * | 2/2011 | Matsumoto et al. | 382/118 |
| 2011/0063571 A1 * | 3/2011 | Duffy | 351/239 |
| 2011/0065069 A1 * | 3/2011 | Duffy | 434/156 |
| 2012/0021390 A1 * | 1/2012 | Dodd | 434/185 |
| 2012/0329018 A1 * | 12/2012 | Katz et al. | 434/236 |
| 2014/0049462 A1 * | 2/2014 | Weinberger et al. | 345/156 |
| 2014/0356822 A1 * | 12/2014 | Hogue et al. | 434/185 |
| 2015/0099946 A1 * | 4/2015 | Sahin | 600/301 |

* cited by examiner

SYSTEM AND METHOD FOR IMPROVING PRESENTATION SKILLS

CROSS-REFERENCE TO RELATED APPLICATIONS

This application claims priority to U.S. Provisional Patent Application No. 61/833,303 filed on Jun. 10, 2013, which is incorporated by reference as if set forth herein in its entirety.

FIELD OF THE INVENTION

A system and method provides improved human presentation skills and, more particularly, increases eye contact, speech fluency, presentation skills, and vocabulary of persons with Autism Spectrum Disorders (ASD).

BACKGROUND OF THE INVENTION

Individuals, especially young adults and older teens afflicted with ASD, often have problems communicating with other individuals, especially with audiences or groups of people. For many individuals with ASD, the consequences of the disorder may manifest as, inter alia, difficulties in making eye-to-eye contact, in presenting ideas fluently, and in socializing and engaging with others. The short- and long-term effect of these social skills deficits may hinder the individual's relationship development, academic success, and professional advancement.

Some commercially-available software applications ("apps") for speech-making and presentations typically only focus on one aspect, e.g., improving language skills, improving reading skills, or the like. One problem with these apps is that, although individuals with ASD can generally use technology well, they often have difficulty applying lessons learned from the app to real-life situations. Other apps for individuals with ASD are targeted for use by caretakers, rather than by the afflicted individuals themselves.

BRIEF SUMMARY OF THE INVENTION

Accordingly, it is desirable to provide a system and method for improving presentation skills, especially skills of individuals with social skill and communication disorders such as Autism. More specifically, it is desirable to provide a system and method for improving presentation skills by targeting more than one aspect of making a presentation, i.e., delivering a speech to an audience, with particular focus on improving eye contact skills, especially among higher functioning individuals who recognize their own social anxiety and desire self-improvement in that area. Moreover, it is desirable to provide a user-friendly system and method that enables higher-functioning individuals with ASD to overcome the anxiety of making eye contact with an audience of one or multiple individuals by practicing the presentation, e.g., speech, using visual prompts in the text of the script of the presentation.

It is particularly desirable to integrate technology and/or apps for tracking the eye movement of a user over time, especially at discrete times within the presentation script. It is also desirable to enable system and method users to record, e.g., make a video, and to time themselves making the presentation while rehearsing the speech. Also desirable is to include speech-to-text technology and/or apps to monitor the diction and fluency of the user during rehearsals, to identify any problems with, for example, enunciation, elision, fluency, and adherence to the presentation script.

In a first aspect of a method for improving social and presentation skills of persons with an Autism Spectrum Disorder, each of the persons has a client device that includes a processing device, memory, a user interface, and a display device. In some embodiments, the method includes rendering and displaying on the display device a presentation script for an oral presentation to be made by a user; monitoring eye movement of the user during the oral presentation to measure at least one of a user's pupil movement and a user's gaze direction; displaying, e.g., on a separate display screen and/or an upper portion of the display device, an indicia, e.g., an image of an eye and/or a pair of eyes, which may periodically change; periodically displaying within the presentation script a visual prompt to cue the user to look at the indicia; measuring eye movement, e.g., using eye tracking software and/or an eye tracking device, at occurrence of the visual prompt; and evaluating whether the user made eye contact with the indicia when prompted. In variations of the embodiment, the method may further include enabling the user to set a timing of the oral presentation and/or enabling the user to record images, e.g., video images, of the user practicing the oral presentation.

In further variations, the method may include providing speech-to-text technology to convert words spoken by the user during the oral presentation to a word-based text; recording the word-based text during the oral presentation; monitoring user diction and user fluency using the speech-to-text technology; comparing the recorded word-based text with the presentation script to identify any oral delivery mistakes; recording instances of any oral delivery mistakes; alerting the user of any oral delivery mistakes; recording instances when the user did not make eye contact with the indicia when prompted; and/or allowing the user to customize the indicia.

In a second aspect, the present invention relates to an apparatus for improving social and presentation skills of users. In some embodiments, the apparatus may include memory for storing computer readable instructions, which, when executed by a processor, create an instance of an application operating on a mobile device; a user interface; a display device; an eye tracking device; and a processing device for executing some of the stored computer readable instructions. In some variations of the embodiment, executing may include rendering and displaying on the display device a presentation script for an oral presentation to be made by a user; monitoring eye movement of the user during the oral presentation, using the eye tracking device, to measure a user's pupil movement and/or a user's gaze direction; displaying on an upper portion of the display device an indicia, e.g., an eye and/or a pair of eyes, which can be changed periodically; periodically displaying within the presentation script a visual prompt to cue the user to look at the indicia; measuring eye movement, using the eye tracking device, at occurrence of the visual prompt; and evaluating whether the user made eye contact with the indicia when prompted. In variations, executing may further include enabling the user to set a timing of the oral presentation and/or enabling the user to record images, e.g., video images, of the user practicing the oral presentation.

In further variations, the apparatus may also include speech-to-text technology to convert words spoken by the user during the oral presentation to a word-based text and executing may further include recording the word-based text during the oral presentation; and monitoring user diction and user fluency using the speech-to-text technology. Executing may also include comparing the recorded word-based text with the presentation script to identify any oral delivery mistakes; recording instances of any oral delivery mistakes; alerting the user of any oral delivery mistakes; using recording instances when the user did not make eye contact with the indicia when prompted; and/or allowing the user to customize the indicia.

In a third aspect, a system for improving social and presentation skills of persons with an autism spectrum disorder is disclosed. In some embodiments, the system includes a client device and a remote server that is coupled to the client device via a communication network. In variations of the embodiment, the client device may include memory for storing computer readable instructions, which, when executed by a processor, create an instance of an application operating on a mobile device; a user interface; a display device; an eye tracking device; and a processing device for executing some of the stored computer readable instructions. In some implementations, executing includes: rendering and displaying on the display device a presentation script for an oral presentation to be made by a user; monitoring eye movement of the user during the oral presentation, e.g., using the eye tracking device, to measure a user's pupil movement and/or a user's gaze direction; displaying, e.g., on an upper portion of the display device an indicia, e.g., an eye and/or a pair of eyes; periodically displaying in the presentation script a visual prompt to cue the user to look at the indicia; measuring eye movement, using the eye tracking device, at occurrence of the visual prompt; and evaluating whether the user made eye contact with the indicia when prompted. In other implementations, the remote server may include a user interface that is configured and arranged to enable third parties to view and access data created when the processing device executes some of the stored computer readable instructions; memory for storing computer readable instructions; a user interface; a display device; a processing device for executing some of the stored computer readable instructions; and a data storage device for storing the presentation script, speech-to-text technology to convert words spoken by the user during the oral presentation to a word-based text, video images of the user practicing the oral presentation, a record of the word-based text during the oral presentation, and/or a record of instances of any oral delivery mistakes.

Although the invention is disclosed and described in the context of users who are individuals with ASD, those of ordinary skill in the art can appreciate that the system and method described herein have applicability to all individuals who make presentations to audiences large and small, to all individuals who may have some degree of social anxiety, and to any individuals desiring to hone their oral presentation skills, especially with respect to making improvements to making eye contact with one's audience. Accordingly, the disclosure is not intended to be read narrowly or to be construed as being limited just to that application of the technology described.

BRIEF DESCRIPTION OF THE DRAWINGS

The accompanying drawings are not intended to be drawn to scale. In the drawings, each identical or similar component that is illustrated in various figures is represented by a like numeral. For purposes of clarity, not every component may be labeled in every drawing. In the drawings.

DETAILED DESCRIPTION OF THE INVENTION

A method and system are described for aiding self-motivated users to overcome anxiety in a social setting, especially a social setting in which the user is making an oral presentation, e.g., a speech, to an audience or interviewing one-on-one. Although the disclosed method and system can be used while the user is making the actual presentation, it may be advantageously employed during user rehearsals, when the user is practicing the speech, to build the confidence of the user. For simplicity, the invention will be described being used in and for the latter scenario, which is to say, during rehearsal for a presentation. Those of ordinary skill in the art can appreciate the applicability of the disclosed steps and elements in the former scenario as well.

System

Figure 1A:
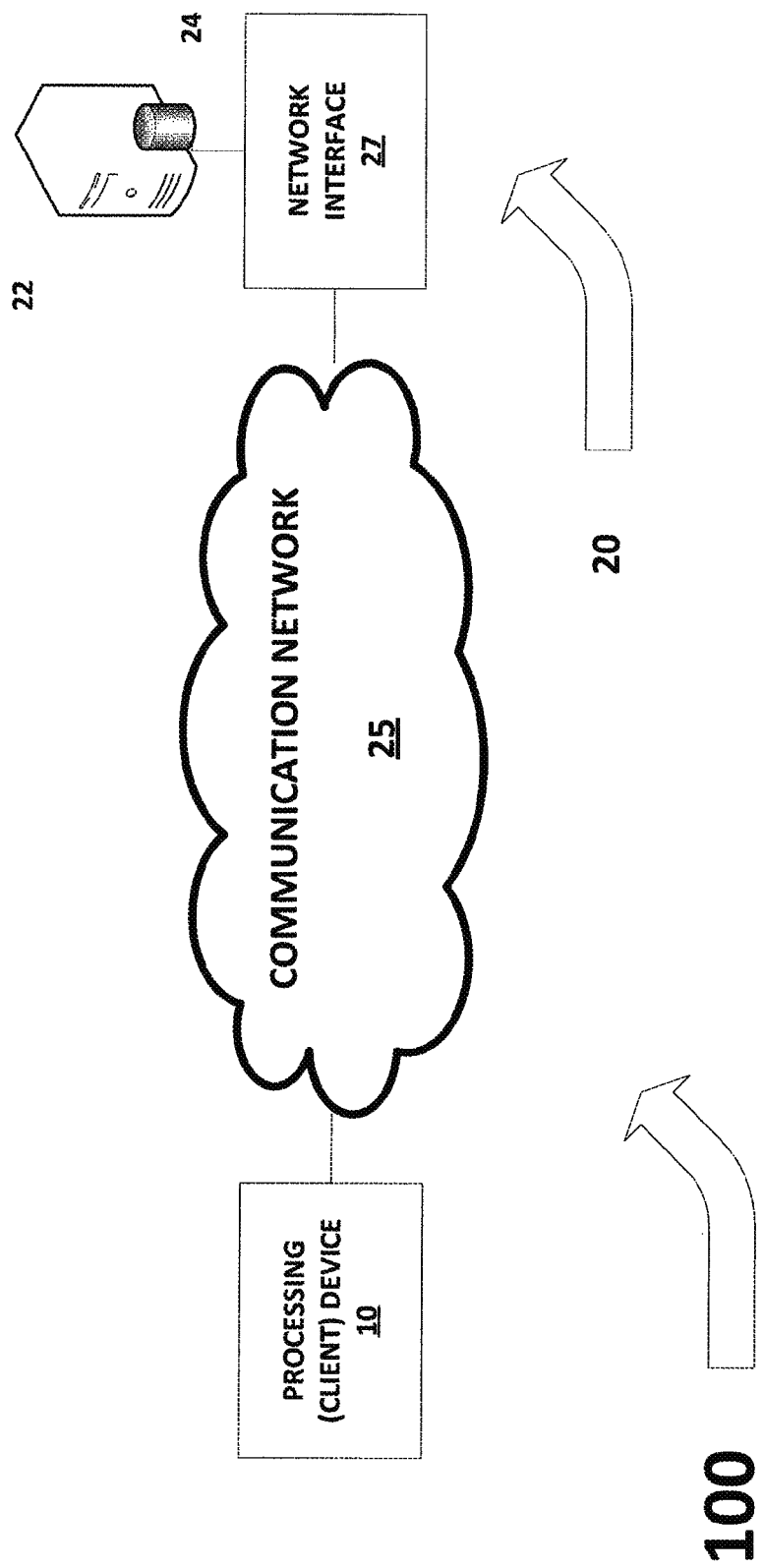
FIG. 1A shows a block diagram of an exemplary system for improving the presentation skills of individuals in accordance with some embodiments of the present invention.
Figure 1B:
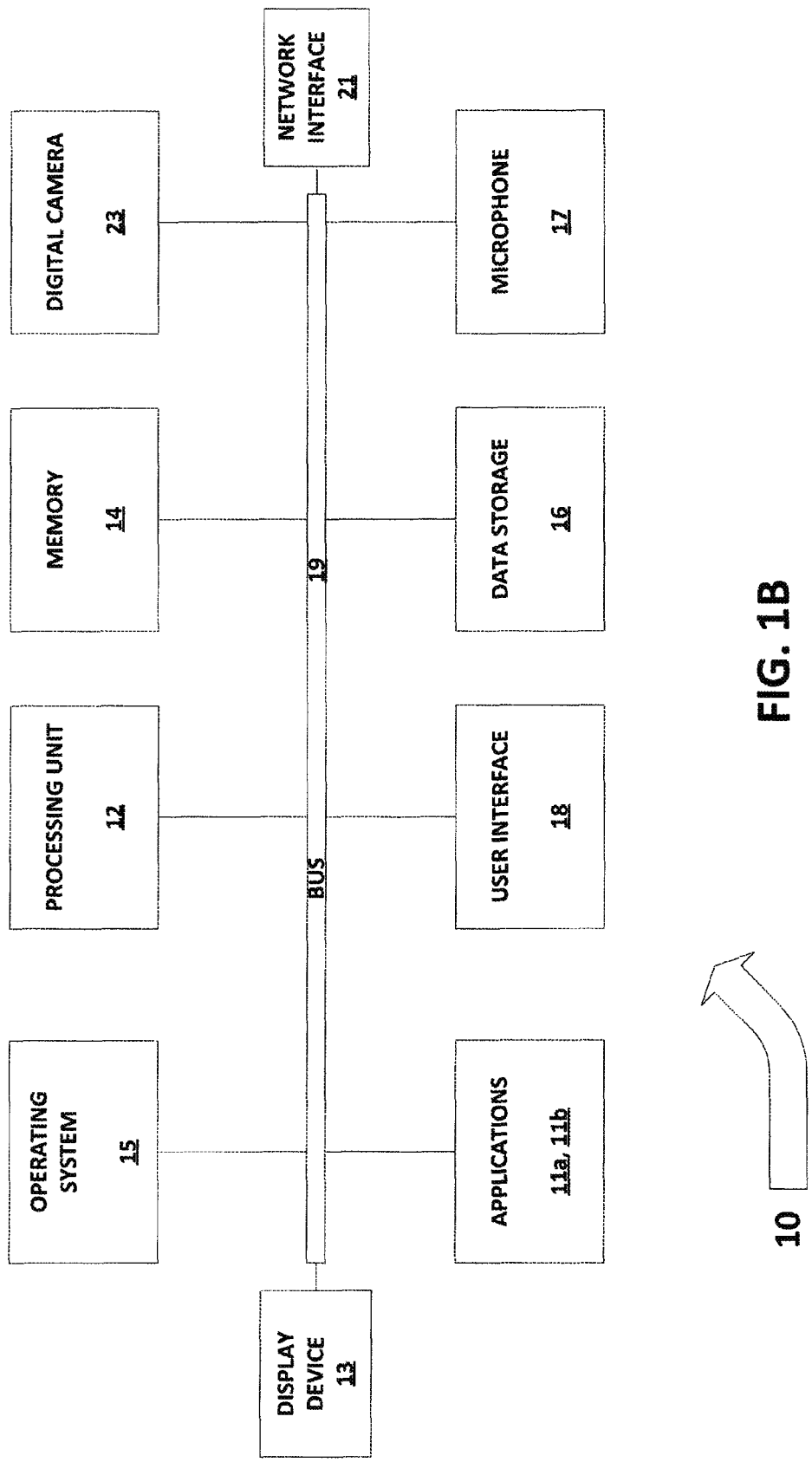
FIG. 1B shows a block diagram of an exemplary apparatus for improving the presentation skills of individuals in accordance with some embodiments of the present invention.

Referring to FIG. 1A and FIG. 1B, there are shown, respectively, exemplary embodiments of a system 100 for improving social and presentation skills of persons with ASD, i.e., users, and a client device 10 adapted for use in that system 100. Preferably, users may practice using any computer system configuration, including hand-held wireless devices such as mobile or cellular telephones, personal digital assistants (PDAs), tablet computers, smartphones, smartpads, smartwatches, Google® glasses, tablet computers, laptop computers, personal computers, gaming systems, multiprocessor systems, microprocessor-based or programmable consumer electronics, minicomputers, mainframe computers, computers running under virtualization, and/or any other computing device that is capable of capturing audio and/or video data.

The data store may be embodied using any computer data store, including but not limited to relational databases, non-relational databases (NoSQL, etc.), flat files, in memory databases, and/or key value stores. Examples of such data stores include the MySQL Database Server or ORACLE Database Server offered by ORACLE Corp. of Redwood Shores, Calif., the PostgreSQL Database Server by the PostgreSQL Global Development Group of Berkeley, Calif., the DB2 Database Server offered by IBM, Mongo DB, Cassandra, and Redis.

The invention may be practiced using any computer or processing system 100 that may include a general purpose computing or processing device, i.e., client device 10, including a processing unit 12, a system memory 14, a data storage medium 16, and a system bus 19 that couples various system components including the system memory 14 to the processing unit 12.

Client devices 10 typically include a variety of computer readable media that can form part of the system memory 14 and be read by the processing unit 12. By way of example, and not limitation, computer readable media may include computer storage media and/or communication media. The system memory 14 may include computer storage media in the form of volatile and/or nonvolatile memory, such as read only memory (ROM) and random access memory (RAM). A basic input/output system (BIOS), containing the basic routines that help to transfer information between components, such as during start-up, is typically stored in ROM. RAM typically contains data and/or program modules that are immediately accessible to and/or presently being operated on by processing unit 12. The data or program modules may include an operating system 15, application programs 11, other program modules, and program data. The operating system 15 may be or include a variety of operating systems such as Microsoft Windows® operating system, the Unix operating system, the Linux operating system, the Mac OS operating system, Google Android operating system, Apple iOS operating system, or another operating system or platform.

At a minimum, the memory 14 may include at least one set of instructions that is either permanently (non-volatile) or temporarily (volatile) stored. The processing unit 12 executes the instructions that are stored in order to process data. The set of instructions may include various instructions that perform a particular task or tasks. Such a set of instructions for performing a particular task may be characterized as a program, software program, software, engine, module, component, mechanism, or tool.

The client device 10 may include a plurality of software processing modules stored in the memory 14 as described above and executed on the processing unit 12 in the manner described herein. The program modules may be in the form of any suitable programming language, which is converted to machine language or object code to allow the processor or processing units 12 to read the instructions. That is, written lines of programming code or source code, in a particular programming language, may be converted to machine language using a compiler, assembler, or interpreter. The machine language may be binary coded machine instructions specific to a particular computer.

Any suitable programming language may be used in accordance with the various embodiments of the invention. Illustratively, the programming language used may include assembly language, Basic, C, C++, CSS, HTML, Java, SQL, Perl, Python, Ruby and/or JavaScript, for example. Further, it is not necessary that a single type of instruction or programming language be utilized in conjunction with the operation of the system and method of the invention. Rather, any number of different programming languages may be utilized as is necessary or desirable.

Also, the instructions and/or data used in the practice of the invention may utilize any compression or encryption technique or algorithm, as may be desired. An encryption module might be used to encrypt data. Further, files or other data may be decrypted using a suitable decryption module.

A user may enter commands and information into the client device 10 through a user interface 18 that includes input devices such as a keyboard and pointing device, commonly referred to as a mouse, trackball or touch pad. Other input devices may include a microphone, joystick, game pad, satellite dish, scanner, voice recognition device, keyboard, touch screen, toggle switch, pushbutton, or the like. These and other input devices are often connected to the processing unit 12 through a user input interface 18 that is coupled to the system bus 19, but may be connected by other interface and bus structures, such as a parallel port, game port or a universal serial bus (USB).

The computing environment may also include other removable/non-removable, volatile/nonvolatile computer storage media 16. For example, a hard disk drive may read or write to non-removable, nonvolatile magnetic media. A magnetic disk drive may read from or writes to a removable, nonvolatile magnetic disk, and an optical disk drive may read from or write to a removable, nonvolatile optical disk such as a CD-ROM or other optical media. Other removable/non-removable, volatile/nonvolatile computer storage media 16 that can be used in the exemplary operating environment include, but are not limited to, magnetic tape cassettes, flash memory cards, digital versatile disks, digital video tape, solid state RAM, solid state ROM, Storage Area Networking devices, solid state drives, and the like. The storage media 16 are typically connected to the system bus 19 through a removable or non-removable memory interface.

The processing unit 12 that executes commands and instructions may be a general purpose computer, but may utilize any of a wide variety of other technologies including a special purpose computer, a microcomputer, mini-computer, mainframe computer, programmed micro-processor, micro-controller, peripheral integrated circuit element, a CSIC (Customer Specific Integrated Circuit), ASIC (Application Specific Integrated Circuit), a logic circuit, a digital signal processor, a programmable logic device such as an FPGA (Field Programmable Gate Array), PLD (Programmable Logic Device), PLA (Programmable Logic Array), RFID integrated circuits, smart chip, or any other device or arrangement of devices that is capable of implementing the steps of the processes of the invention.

One or more monitors or display devices 13 may also be connected to the system bus 19, e.g., via an interface. In addition to display devices 13, the client device 10 may also include other peripheral output devices, which may be connected through an output peripheral interface. The client device 10 implementing the invention may operate in a networked environment using logical connections to one or more remote computers. The remote computers typically including many or all of the elements described above.

It should be appreciated that the processing units 12 and/or memories 14 need not be physically in the same location. For example, in some implementations, the system 100 may also include a general purpose computing or processing device, i.e., server device 20, including a processing unit 22, a system memory 24, a data storage medium, and a system bus. Hence, each of the processing units 12, 22 and each of the memories 14, 24 used by the system 100 may be in geographically distinct locations and be connected so as to communicate with each other in any suitable manner. Additionally, it is appreciated that each of the processing units 12, 22 and/or memories 14, 24 may be composed of different physical pieces of equipment.

The devices 10, 20 that embody the invention may communicate with the user via notifications sent over any protocol that can be transmitted over a packet-switched network or telecommunications ("communication") network 25. By way of example, and not limitation, these may include SMS messages, email (SMTP) messages, instant messages (GChat, AIM, Jabber, etc.), social platform messages (Facebook posts and messages, Twitter direct messages, tweets, retweets, etc.), and mobile push notifications (iOS, Android).

It is understood that the methods and systems 100 described may contain software, middleware, hardware, and any combination thereof connected to, coupled with, and/or in communication with a communication network 25, e.g., the World Wide Web, the Internet, a local area network (LAN), a wide area network (WAN), and so forth. Computing/processing devices 10, 20 are capable of communicating with each other via the communication network 25, and it should be appreciated that the various functionalities of the components may be implemented on any number of devices.

The invention may be practiced using any communications network 25 capable of transmitting Internet protocols. A communications network 25 generally connects a client device 10 with a server device 20, and in the case of peer-to-peer communications, connects two peers. The communication may take place via any media such as standard telephone lines, LAN or WAN links (e.g., T1, T3, 56 kb, X.25), broadband connections (ISDN, Frame Relay, ATM), wireless links (802.11, Bluetooth, 3G, CDMA, etc.), and so on. The communications network 25 may take any form, including but not limited to LAN, WAN, wireless (WiFi, WiMAX), or near field (RFID, Bluetooth). The communications network 25 may use any underlying protocols that can transmit Internet protocols, including but not limited to Ethernet, ATM, VPNs (PPPoE, L2TP, etc.), and encryption (SSL, IPSec, etc.).

Examples of software apps that may be used in connection with the system 100 include an eye-tracking app 11a and/or a speech-to-text app 11b. The eye-tracking app 11a provides a device that is configured to track, i.e., to measure the location and the changes of location, the movement of either or each of the user's eyes. Such movement may be used to evaluate whether or not the user made eye contact with a "virtual audience" indicia in response to a prompt appearing in the presentation script. The movement may be measured by a change in distance, e.g., in micrometers, and/or by a change of a point of focus, e.g., in degrees. Representative, commercially-available eye tracking apps include EyeWorks™ from EyeTracking, Inc. of San Diego, Calif. and S2 Eye Tracker from Mirametrix, Inc. of Montreal, Canada. The speech-to-text app 11b provides a device that is adapted to make a digital textual record of the user's oral presentation of the presentation script being rehearsed. This textual record may then be compared to the presentation script, e.g., word for word, to identify a word(s) and/or a script portion(s) in the presentation script that the user has difficulty speaking and that a listener would have difficulty understanding, or that the user missed or skipped. These identified words or script portions may then be given greater attention in subsequent rehearsals. Representative, commercially-available speech-to-text apps include the AT&T Speech API from AT&T, the HTML5 Speech API from Mozilla Corporation of Mountain View, Calif., the Text to Speech API from iSpeech, Inc. of Newark, N.J., and the Dragon speech recognition software from Nuance Communications, Inc, of Burlington, Mass.

In some variations, the client device 15 may include an image-recording device 23, e.g., a digital camera or video recorder, and/or an audio-recording device 17, e.g., a microphone. In some variations, the image-recording device 23 may be in electronic communication with the processing unit 12, data storage medium 14, and user interface 18 for storing the image data locally, e.g., on the client device 10, and/or with a communication network interface 21 for storing the image remotely, e.g., at the server device 20. Alternatively, the image data taken by the digital camera 23 may be uploaded onto a removable memory device, e.g., a memory stick, flash drive, or the like, and subsequently downloaded onto the processing unit that is in electronic communication with a data storage medium, a communication network interface, or the like. Similarly, the audio-recording device 17 may be in electronic communication with the processing device 12, data storage medium 14, and user interface 18 for storing the audio data locally, e.g., on the client device 10, and/or with a communication network interface 21 for storing the audio data remotely, e.g., at the server device 20. Alternatively, the audio data recorded by the microphone 17 may be uploaded onto a removable memory device, e.g., a memory stick, flash drive, or the like, and subsequently downloaded onto a processing unit that is in electronic communication with a data storage medium, a communication network interface, and the like.

Method

Having described a client device 10 and a system 100 for improving social and presentation skills in persons with ASD, a method using the device 10 and system 100 will now be described. Those of ordinary skill in the art can appreciate that the method is not to be construed as being practiced simply by the client device 10 and system 100 described hereinabove. Indeed, there are a myriad of devices having a processing device, memory, a user interface, and a display device that can be programmed or structured and arranged to perform the steps described in greater detail below. Moreover, although the method will be described for persons having ASD, those of ordinary skill in the art can appreciate the applicability of the invention to all persons wishing to improve their social and presentation skills.

Figure 2:
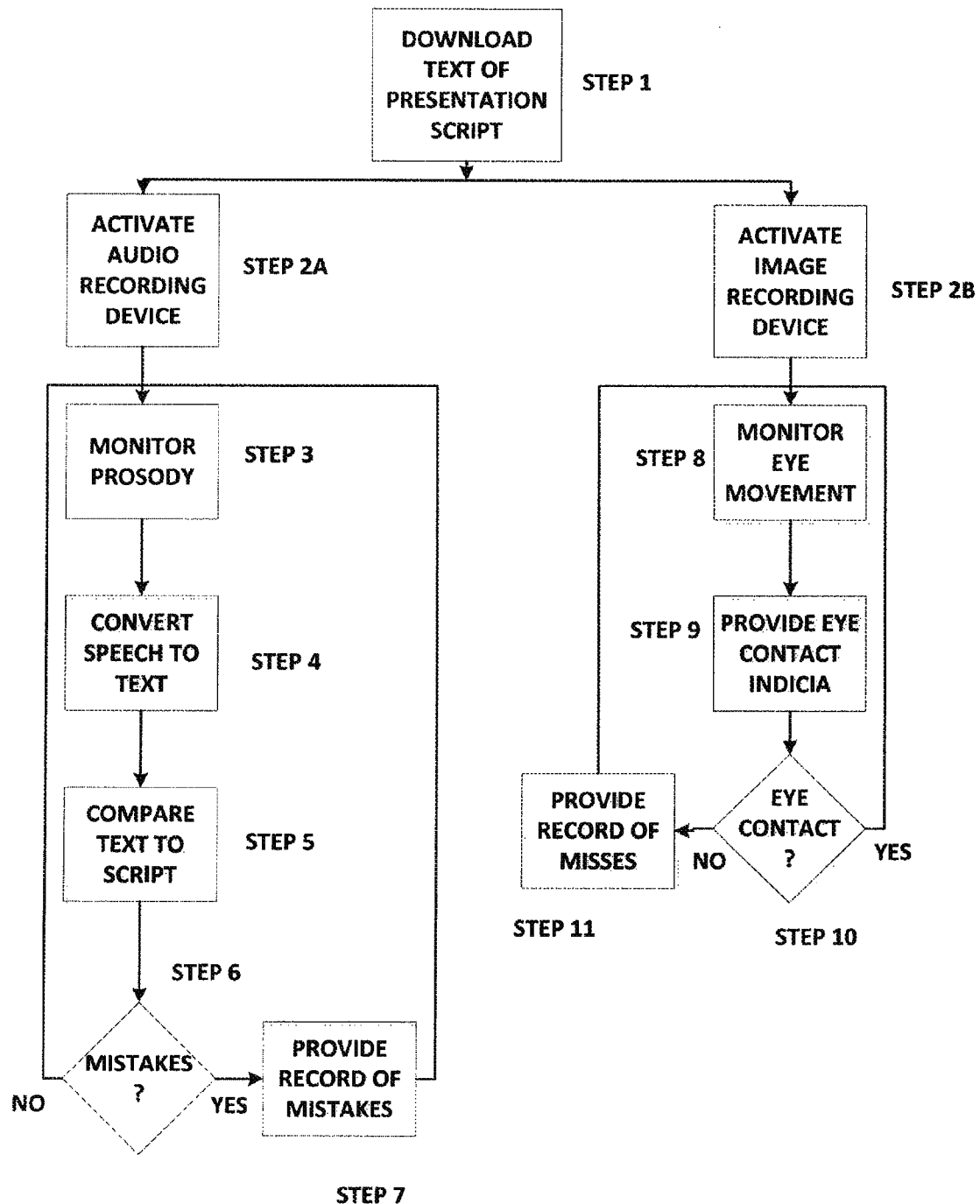
FIG. 2 shows a flow diagram of an exemplary method for improving the presentation skills of individuals in accordance with some embodiments of the present invention.

Referring to FIG. 2, there is shown a flow chart of one exemplary embodiment of a method for improving social and presentation skills of persons with ASD. In some embodiments, the user is equipped with a client device having a processing device, memory, a user interface, and a display device. Preferably, the memory includes computer-readable instructions that are executable by the processing device. In a first step, prior to rehearsing and/or making a presentation, the user or a third party on the user's behalf may download a presentation script into a data file stored in the client device (STEP 1). Alternatively, the presentation script can be downloaded in a data file in the remote server device, in which case, the remote server device is adapted to upload the presentation onto the user's client device. In another alternative, the user may import the data of the presentation script from, for example, Dropbox™ or some other cloud-based data storage that allows members to store and share files and other data.

Contemporaneously with rehearsing and/or making a presentation, an image-recording device (STEP 2B) and/or an audio-recording device (STEP 2A) may be activated. Activation may include recording video and audio data of the user while she is rehearsing or making a presentation and, further, storing the video data and audio data in data storage provided expressly therefor. Data storage may occur locally, i.e., on the client device, or remotely, i.e., on the server device and/or on Dropbox™ or other cloud-based data storage. Once again, the user or a third party on the user's behalf may activate one or both of the recording devices (STEP 2A, STEP 2B). Third parties may include, for the purpose of illustration and not limitation, medical professionals, speech therapists, teachers, parents, guardians, and so forth.

With the image and audio-recording devices recording image and storing video data and audio data, the client device and/or the remote server device may render and display, e.g., on the display device of the client device, the downloaded or uploaded presentation script. The display may advantageously include a scrolling feature that can be adjusted to the user's rate of delivery. As the user "speaks the speech," in addition to being recorded, the user's prosody may be monitored (STEP 3) and further converted to a word-based text (STEP 4), e.g., using speech-to-text technology. As the speech-to-text technology converts the user's speech to word-based text (STEP 4), the processing unit may compare, e.g., word for word, the word-based text to the downloaded presentation script (STEP 5). The comparison (STEP 5) identifies mistakes (STEP 6), e.g., clarity, diction, enunciation, fluency, adherence to the script, and the like.

Advantageously, any mistakes identified (STEP 6) may be identified and recorded (STEP 7) for providing feedback to the user. In some implementations, the processing device of the client device may also provide, e.g., transmit, an alert message to the user. By recording individual oral delivery mistakes, the user may focus further attention on and dedicate future rehearsal time to that portion(s) of the presentation, without having to practice the entire presentation. Records of mistakes may also be accessed by or made accessible to third parties, e.g., speech therapists, teachers, and the like, to enable the third parties to work with the user in a targeted, constructive manner.

Also, while the user is rehearsing or making an oral presentation, the image-recording device, e.g., a digital camera, records the user (STEP 2B) rehearsing or making the oral presentation. Contemporaneous with recording video image data, an eye tracking and/or monitoring device, e.g., eye tracing software, may monitor the user's eye movement and/or gaze direction (STEP 8). For example, the eye tracking and/or monitoring device may measure the user's pupil movement to track the user's progress through the presentation script. Instances in which the user's pupil movement remains fixed at a certain location in the script for a predetermined period of time may be identified and recorded for providing feedback to the user. In some implementations, the processing unit of the client device may also provide, e.g., transmit, an alert message to the user. Records of lack of eye movement may also be accessed by or made accessible to third parties, e.g., speech therapists, teachers, and the like, to enable the third parties to work with the user in a targeted, constructive manner.

Figure 3:
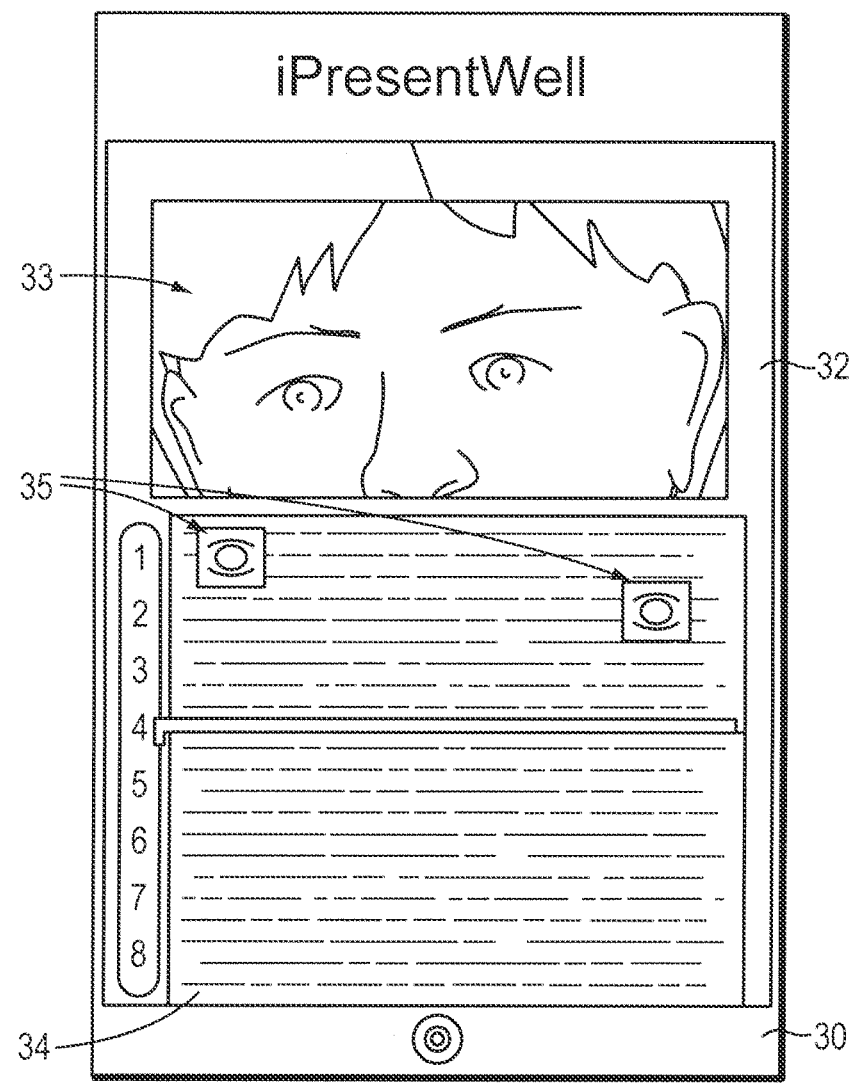
FIG. 3 shows an illustrative embodiment of a screen shot on the display device of a user's client device in accordance with an embodiment of the present invention.

Advantageously, periodically during the oral rehearsal or presentation, the processing unit may integrate a prompt or cue into the presentation script (STEP 9). This visual prompt (STEP 9) may be provided to cue the user to establish eye contact with her audience. During rehearsal of an oral presentation, in which the presence of an audience is not likely, the prompt is meant to cue the user to look at some indicia displayed, for example, on an upper or other portion of the display device or, alternatively, on a separate display device. Illustrative examples of the indicia at which the user is expected to direct her gaze and/or to move her eyes towards can include an image of a human eye, a pair of eyes, a pair of eyes with a human forehead, a face, a group of faces, and so forth. In some implementations, the indicia can change repeatedly, e.g., be looped, so that at each prompt the user's gaze is directed to a new eye or set of eyes. FIG. 3 illustrates an illustrative embodiment of a screen shot showing the user's client device 30 having a display device 32 on which the presentation script 34 is rendered and displayed. Visual prompts 35 appear at discrete locations of the presentation script 34. Indicia, in this case a pair of eyes 33, appear at the top of the display device 32.

To evaluate whether or not the user has made eye contact with the "visual audience," i.e., the pair of eyes indicia, when prompted, the user's eye movement may be measured, e.g., using the eye tracking and monitoring device, at occurrence of the visual prompt. The measurement device is sufficiently accurate to determine whether or not the user has made eye contact (STEP 10) with her "virtual audience," i.e., the pair of eyes indicia. Advantageously, any missed opportunities for making prompted eye contact ("misses") may be identified and recorded (STEP 11) for providing feedback to the user. In some implementations, the processing device of the client device may also provide, e.g., transmit, an alert message to the user. Records of eye contact misses may advantageously be accessed by or made accessible to third parties, e.g., speech therapists, teachers, and the like, to enable the third parties to work with the user in a targeted, constructive manner.

Additional features of the method may include enabling the user to time the oral presentation, e.g., using a timing device in communication with the processing unit of the client device and/or enabling the user to customize her "virtual audience." For example, in some implementations, users may be able to make or import their own images for use as indicia, to use images of people with whom they are more familiar, e.g., parents, siblings, and the like. Users may also be able to turn off the "virtual audience" feature. The method may also include a reward feature by which the user or a third party may establish a goal for a particular rehearsal and/or rewards may be based on the number of times the user rehearses the oral presentation or improves in her performance in the oral presentation. If the user accomplishes the goal or performs a certain number of rehearsals, she may receive a reward such as an iTune download, a Kiip reward, a discount coupon, and so forth. Audio and video data captured during a rehearsal may also be exported to an online video website, e.g., YouTube.

Additional uses of the method and system described herein may facilitate providing the user with experience involving open-ended dialog exchange, such as at a job interview or meeting new individuals at a social event.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology.

The invention claimed is:

1. A method for improving social and presentation skills of a person, the person having a client device including a processing device, memory, a user interface, and a display device, the method comprising:
   rendering and displaying on the display device a scrolling presentation speech for an oral presentation to be made by a user;
   monitoring eye movement of the user during the oral presentation to measure at least one of a user's pupil movement and a user's gaze direction;
   displaying an indicia on at least one of a separate display screen and a portion of the display device;
   periodically displaying within the scrolling presentation speech a visual prompt to cue the user to look at the indicia;
   measuring eye movement at occurrence of the visual prompt; and
   evaluating whether the user made eye contact with the indicia when prompted.

2. The method of claim 1 further comprising setting a timing of the oral presentation.

3. The method of claim 1 further comprising recording images of the user practicing the oral presentation.

4. The method of claim 3 further comprising recording video images of the user practicing the oral presentation.

5. The method of claim 1 further comprising:
   converting words spoken by the user during the oral presentation to a word-based text;
   recording the word-based text during the oral presentation; and
   monitoring at least one of user diction and user fluency.

6. The method of claim 5 further comprising:
   comparing the recorded word-based text with the presentation speech to identify any oral delivery mistakes; and
   recording instances of any oral delivery mistakes.

7. The method of claim 6 further comprising alerting the user of any oral delivery mistakes.

8. The method of claim 1, wherein measuring eye movement includes using at least one of eye tracking software and an eye tracking application.

9. The method of claim 1, wherein displaying the indicia includes periodically changing an image displayed.

10. The method of claim 1 further comprising recording instances when the user did not make eye contact with the indicia when prompted.

11. The method of claim 1 further comprising allowing the user to customize the indicia.

12. An apparatus for improving social and presentation skills of persons, the apparatus comprising:
   memory for storing computer readable instructions, which, when executed by a processing unit, create an instance of an application operating on a mobile device;
   a user interface;
   a display device;
   an eye tracking device; and
   a processing unit for executing some of the stored computer readable instructions, wherein executing comprises:
      rendering and displaying on the display device a scrolling presentation speech for an oral presentation to be made by a user;
      monitoring eye movement of the user during the oral presentation, using the eye tracking device, to measure at least one of a user's pupil movement and a user's gaze direction;
      displaying on a portion of the display device an indicia;
      periodically displaying within the scrolling presentation speech a visual prompt to cue the user to look at the indicia;
      measuring eye movement, using the eye tracking device, at occurrence of the visual prompt; and
      evaluating whether the user made eye contact with the indicia when prompted.

13. The apparatus of claim 12, wherein executing further comprises setting a timing of the oral presentation.

14. The apparatus of claim 12, wherein executing further comprises recording images of the user practicing the oral presentation.

15. The apparatus of claim 14, wherein executing further comprises recording video images of the user practicing the oral presentation.

16. The apparatus of claim 12 further comprising converting words spoken by the user during the oral presentation to a word-based text, wherein executing further comprises:
   recording the word-based text during the oral presentation; and
   monitoring at least one of user diction and user fluency.

17. The apparatus of claim 16, wherein executing further comprises:
   comparing the recorded word-based text with the presentation speech to identify any oral delivery mistakes; and
   recording instances of any oral delivery mistakes.

18. The apparatus of claim 17, wherein executing further comprises alerting the user of any oral delivery mistakes.

19. The apparatus of claim 12, wherein executing further comprises recording instances when the user did not make eye contact with the indicia when prompted.

20. The apparatus of claim 12, wherein executing further comprises allowing the user to customize the indicia.

21. A system for improving social and presentation skills of persons, the system comprising:
   a client device further comprising:
      memory for storing computer readable instructions, which, when executed by a processing unit, create an instance of an application operating on a mobile device;
      a user interface;
      a display device;
      an eye tracking device; and
      a processing unit for executing some of the stored computer readable instructions, wherein executing comprises:
         rendering and displaying on the display device a scrolling presentation speech for an oral presentation to be made by a user,
         monitoring eye movement of the user during the oral presentation, using the eye tracking device, to measure at least one of a user's pupil movement and a user's gaze direction,
         displaying on a portion of the display device an indicia,
         periodically displaying in the scrolling presentation speech a visual prompt to have the user look at the indicia,
         measuring eye movement, using the eye tracking device, at occurrence of the visual prompt, and
         evaluating whether the user made eye contact with the indicia when prompted; and
   a remote server that is coupled to the client device via a communication network.

22. The system of claim 21, wherein the remote server comprises a user interface that is configured and arranged to enable third parties to view and access data created when the processing unit executes at least some of the stored computer readable instructions.

23. The system of claim 21, wherein the remote server comprises:
   memory for storing computer readable instructions;
   a user interface;
   a display device;
   a processing unit for executing at least some of the stored computer readable instructions; and
   a data storage device for storing at least one of the presentation speech, speech-to-text technology to convert words spoken by the user during the oral presentation to a word-based text, video images of the user practicing the oral presentation, a record of the word-based text during the oral presentation, and a record of instances of any oral delivery mistakes.

* * * * *